May 6, 1958 A. H. BECK Plant Pat. 1,699
AZALEA
Filed Oct. 17, 1957
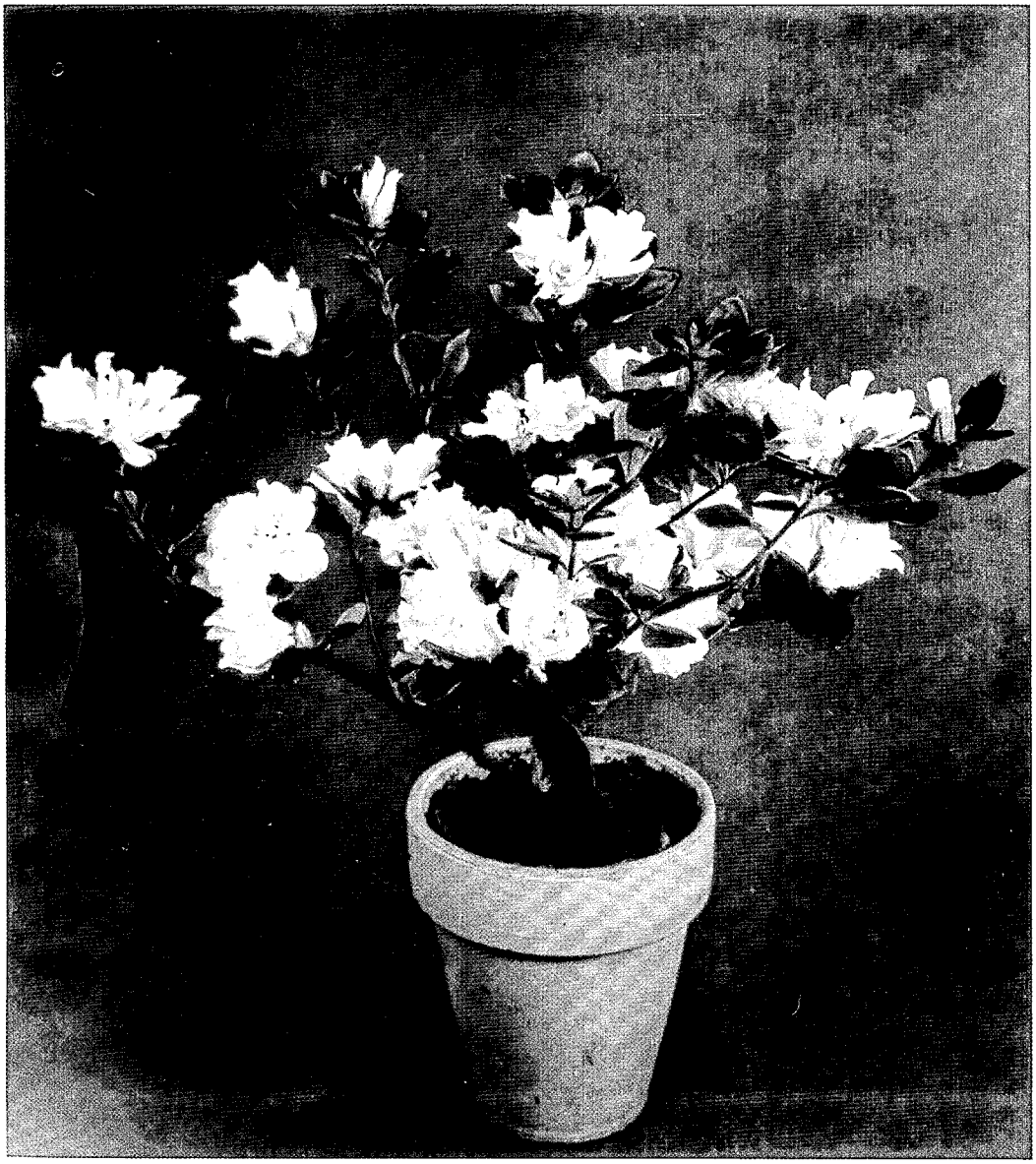

United States Patent Office

Plant Pat. 1,699
Patented May 6, 1958

1,699

AZALEA

Arthur H. Beck, Glenolden, Pa., assignor to Vosters Nurseries and Greenhouses, Inc., Secane, Pa., a corporation of Pennsylvania Application October 17, 1957, Serial No. 690,881

1 Claim. (Cl. 47—60)

This invention relates to a new and distinct variety of azalea plant of the Kurume type, believed to be a sport mutation of Hinodegeri, an unpatented variety, having the characteristic growing features of Hinodegeri to the extent that cuttings that have the tip retained will set buds regardless of the time of year when made.

This new variety was originated and discovered by me in a glass house under my supervision and control at Secane, Delaware County, Pennsylvania. It has been carefully watched, cultivated and nurtured by me and has been asexually reproduced by me and under my supervision in the glass house, by rooting cuttings from the original new plant and by rooting cuttings from each of 3 successive generations of said plant.

Each generation has remained true to its original type and the characteristics described herein through the propagation of 30,000 plants over a period of 2½ years, and has shown its qualities and characteristics to be permanently fixed.

In physical structure the main stem or trunk of the plant, like its parent Hinodegeri, is strong, rugged and sturdy and its many branches grow in irregular directions. However, its branches are much sturdier and stronger than the branches of its parent and its mature ovate shaped leaves are somewhat darker and larger than those of its parent.

The plant, like its parent is an early to midseason blooming variety which blooms once a year with a profusion of flowers, but whereas the flowers of its parent have two corolla, one telescoped within the other (this type of flower being known as hose-in-hose), the flowers of my improved and different plant have three to four larger, deeper colored and shaded corolla or hose telescoped one within the other and appear to be double to triple.

The accompanying drawing illustrates the form and color of a typical specimen of my new variety of azalea plant, the color of which is shown as nearly true as is possible in this type of illustration.

The following is a detailed description of my new variety of azalea plant in which references to the color of the plant are according to Ridgway Color Nomenclature:

*Plant*

Form: Bush—many branches stronger and sturdier than parent; woody stems, Bister XXIX, blended with Rinnemann's Green (Pl. XVIII).

Growth habit: Medium to fast; branching, compact but looser than its parent.

Rooting: Vigorous; compact.

Blooming habit: Free, resulting in a profusion of blooms.

Blooming season: Early in midseason.

Foliage:

*Size.*—Medium to large.

*Quantity.*—Abundant.

*Color.*—Dark Dull Yellow Green (Pl. XXXII).

*Shape.*—Ovate.

*Texture.*—Top face—glossy; under face—rough.

*Edge.*—Smooth.

*Flowers*

Buds:

*Size.*—About 1½" long and gradually growing in length with unfolding of petals. Rose Doree (Pl. I) blended into Geranium Pink (Pl. I).

*Petals.*—Eosine Pink (Pl. I) lightly blended with Deep Rose Pink (Pl. XII); depth color Rose Doree (Pl. I); marks on throat Rose Color (Pl. XII).

*Set.*—Freely (3 to 4 per branch) and profusely in first year of growth. Other features of bud: permanence; holds form 2 to 3 weeks before fully opened.

Bloom:

*Size.*—Large and full averaging about 2 inches between opposite tips of petals.

*Arrangement.*—Three to four blooms in a cluster on strong medium length stems.

*Form.*—Three to four corolla to each bloom; double to triple.

*Color.*—Eosine Pink (Pl. I) blended with Deep Rose Pink (Pl. XII); depth color Rose Doree (Pl. I); marks on throat Rose Color (Pl. XII).

*Shape.*—Medium to long depth. Other features of bloom: performanence.

Genital organs:

*Stamens.*—Five to seven in number; anthers—Claret Brown (Pl. I).

*Filaments.*—La France Pink (Pl. I).

This plant is a desirable and commercially valuable evergreen azalea of compact form which has deep green leaves and which is particularly characterized by its production of an abundance of multiple type flowers of a deep rose pink color whose fully developed buds hold form for 2 to 3 weeks before fully opened. As full petal-age develops the rose pink color lightens but the deep rose colored throat is retained. Full flowers are retained without edge browning longer than other types.

I claim:

A new and distinct variety of azalea plant substantially as illustrated and described, characterized most particularly by its production of an abundance of multiple type flowers.

No references cited.